(12) United States Patent
Hossner

(10) Patent No.: US 8,088,779 B2
(45) Date of Patent: *Jan. 3, 2012

(54) PYRAZOLO [1,5-ALPHA] PYRIMIDINYL DERIVATIVES USEFUL AS CORTICOTROPIN-RELEASING FACTOR (CRF) RECEPTOR ANTAGONISTS

(75) Inventor: Frank Hossner, Harlow (GB)

(73) Assignee: SmithKline Beecham (Cork) Limited, Currabinny, Carrigaline, County Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 12/067,939

(22) PCT Filed: Sep. 28, 2006

(86) PCT No.: PCT/EP2006/009531
§ 371 (c)(1),
(2), (4) Date: Jul. 9, 2008

(87) PCT Pub. No.: WO2007/039264
PCT Pub. Date: Apr. 12, 2007

(65) Prior Publication Data
US 2008/0306092 A1     Dec. 11, 2008

(30) Foreign Application Priority Data
Sep. 30, 2005  (GB) .................... 0519957.5
Oct. 19, 2005  (WO) ............ PCT/US2005/037576

(51) Int. Cl.
*A01N 43/90*   (2006.01)
*A61K 31/519*  (2006.01)
*C07D 487/00*  (2006.01)
(52) U.S. Cl. .................. 514/259.3; 544/281
(58) Field of Classification Search .............. None
See application file for complete search history.

(56) References Cited

U.S. PATENT DOCUMENTS

| | | | |
|---|---|---|---|
| 6,060,478 A * | 5/2000 | Gilligan et al. ............ 514/228.5 |
| 6,191,133 B1 * | 2/2001 | Coppen ................. 514/249 |
| 7,253,284 B2 | 8/2007 | DiFabio et al. |
| 7,279,474 B2 | 10/2007 | Capelli et al. |
| 7,462,622 B2 | 12/2008 | DiFabio et al. |
| 2003/0139426 A1 | 7/2003 | Wilde et al. |
| 2005/0037576 A1 | 2/2005 | Chen et al. |
| 2007/0004708 A1 | 1/2007 | Andriotti et al. |
| 2007/0021429 A1 | 1/2007 | St. Denis |
| 2007/0066640 A1 | 3/2007 | Castiglioni et al. |
| 2007/0219232 A1 | 9/2007 | DiFabio et al. |
| 2007/0287705 A1 | 12/2007 | Luo et al. |
| 2007/0293511 A1 | 12/2007 | Luo et al. |
| 2008/0064719 A1 | 3/2008 | Lanier et al. |
| 2008/0194589 A1 * | 8/2008 | Lanier et al. ............... 514/259.3 |

FOREIGN PATENT DOCUMENTS

| | | |
|---|---|---|
| GB | 2378702 | 2/2003 |
| WO | WO 2006/044958 | 4/2006 |

* cited by examiner

*Primary Examiner* — Jeffrey Murray
(74) *Attorney, Agent, or Firm* — Bonnie L. Deppenbrock

(57) ABSTRACT

The present invention generally relates to the polymorph Form 2 of [3-(4-methoxy-2-methyl-phenyl)-2,5-dimethyl-pyrazolo[1,5-a]pyrimidin-7-yl]-[(S)-1-(3-methyl-[1,2,4]oxa-diazol-5-yl)-propyl]amine. The present invention also relates to pharmaceutical compositions comprising the same and methods of using the same.

(I)

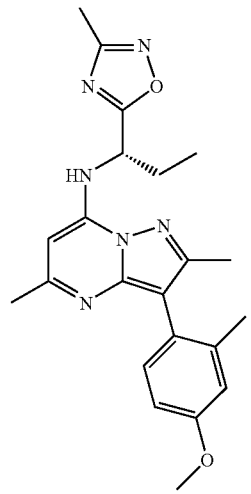

2 Claims, 8 Drawing Sheets

US 8,088,779 B2

PYRAZOLO [1,5-ALPHA] PYRIMIDINYL DERIVATIVES USEFUL AS CORTICOTROPIN-RELEASING FACTOR (CRF) RECEPTOR ANTAGONISTS

This application is a §371 application of PCT/EP2006/009531, filed 28 Sep. 2006, which claims the benefit of GB 0519957.5, filed 20 Sep. 2005, and PCT/US2005/037576, filed 19 Oct. 2005.

BACKGROUND OF THE INVENTION

The present invention generally relates to the polymorph Form 2 of [3-(4-methoxy-2-methyl-phenyl)-2,5-dimethyl-pyrazolo[1,5-a]pyrimidin-7-yl]-[(S)-1-(3-methyl-[1,2,4]oxa-diazol-5-yl)-propyl]-amine. The present invention also relates to pharmaceutical compositions comprising the same and methods of using the same.

Corticotropin releasing factor (CRF) is a 41 amino acid peptide that coordinates the overall response of the body to stress. As an agonist of CRF receptors (e.g., CRF1 and CRF2), CRF is well known as the primary physiological secretagogue controlling hypothalamic-pituitary-adrenal (HPA) axis activity which mediates the endocrine stress response. CRF also plays a central role in the autonomic and behavioural responses to stress. Variation in physiological levels of CRF has been correlated with various disorders including depression and anxiety.

Antagonists of CRF receptors have been shown to effectively ameliorate behavioural stress responses in animal models. It is well established that systemic administration of CRF1 receptor antagonists leads to anxiolytic and antidepressant effects in rodents. Animal model evidence also shows that CRF1 antagonists can help alleviate the symptoms of drug withdrawal, stress-induced seizures, and certain inflammations. A role for CRF has also been postulated in the etiology and pathophysiology of Alzheimer's disease, Parkinson's disease, Huntington's disease, progressive supranuclear palsy, and amyotrophic lateral sclerosis as they relate to the dysfunction of CRF neurons in the central nervous system. Eating disorders, such as anorexia nervosa, have also been linked to elevated levels of CRF.

Though widely dispersed throughout the central nervous system, CRF receptors are also found in peripheral systems including glandular, vascular, gastrointestinal, and immune system tissues. Accordingly, CRF antagonists are believed to have potential in treating numerous other disorders outside the central nervous system.

Some CRF-related disorders of peripheral systems include, for example, hypertension, tachycardia, congestive heart failure, stroke, irritable bowel syndrome, post-operative ileus, and colonic hypersensitivity. Studies have indicated that CRF1 antagonists may also be useful as hair growth stimulators.

The compound [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine has been identified as an effective CRF receptor antagonist that can be useful in treating, for example, the above-named disorders.

This compound is reported in the Internation Patent Application WO2006/044958, which is incorporated herein by reference in its entirety.

While numerous CRF receptor antagonists have been discovered, like the above compound, few typically possess the characteristics that are satisfactory for the preparation of stable pharmaceutical compositions. Melting point, hygroscopicity, stability, solubility, crystallinity, bioavailability, and handling characteristics are among the numerous properties that need to be considered in preparing medicaments that can be effectively administered. Accordingly, there is an ongoing need to prepare compounds with physical and chemical properties that are both physiologically acceptable and suitable for preparing reproducible pharmaceutical formulations. The polymorph of the present invention helps fulfils this and other needs. The polymorph of the present invention is the most thermodynamically stable between the two Forms of [3-(4-methoxy-2-methyl-phenyl)-2,5-dimethyl-pyrazolo[1,5-a]pyrimidin-7-yl]-[(S)-1-(3-methyl-[1,2,4]-oxadiazol-5-yl)-propyl]-amine of Formula (I). In the Experimental Section an experiment of conversion of a mixture of the two forms to the more stable Form 2 and a calculation of the transition temperature will be provided.

DETAILED DESCRIPTION OF THE INVENTION

Figure 1:
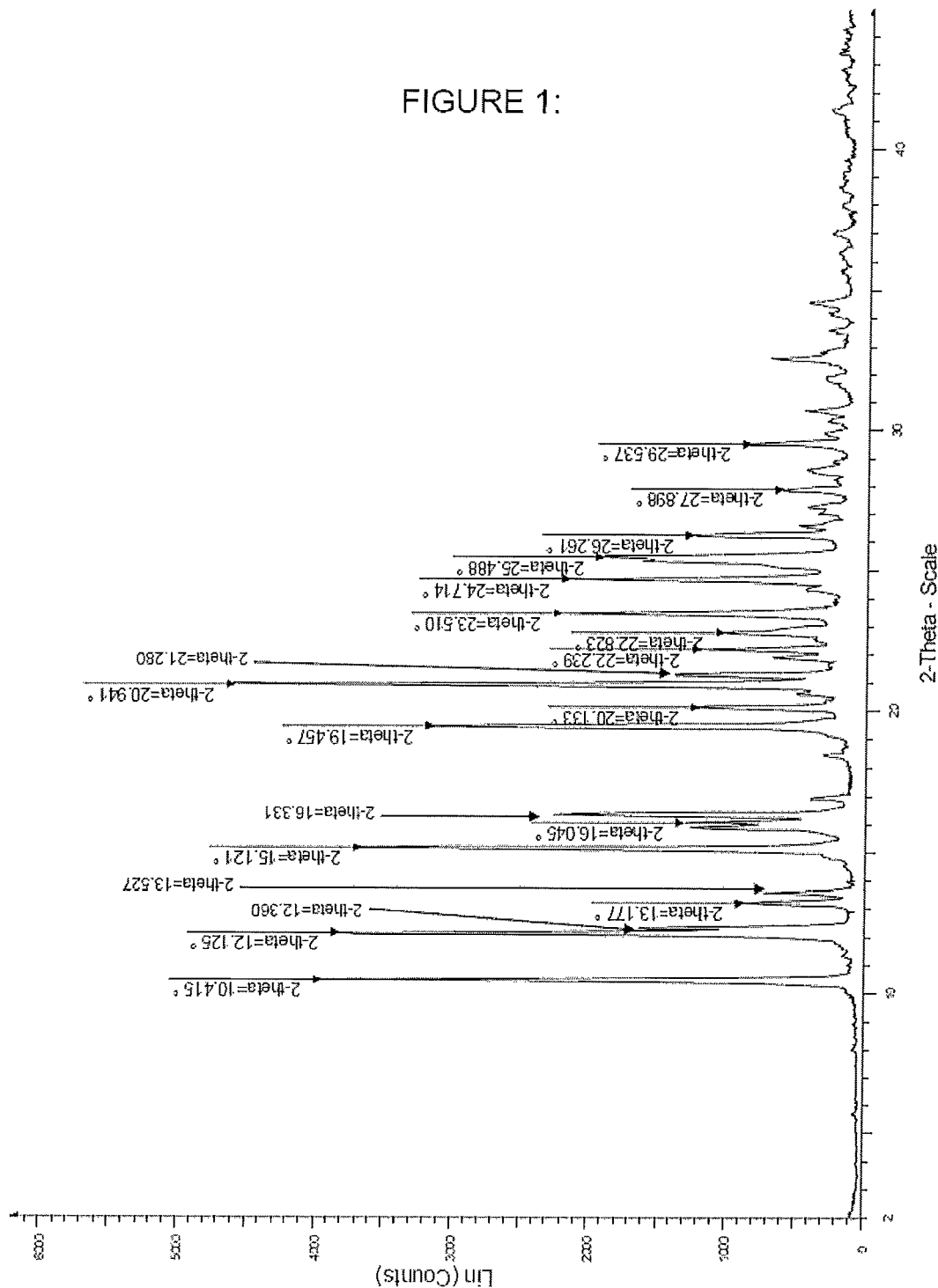
FIG. 1 shows X-Ray powder diffraction data obtained for Form 2 of [3-(4-Methoxy-2-methyl-phenyl)-2,5-dimethyl-pyrazolo[1,5-a]pyrimidin-7-yl]-[(S)-1-(3-methyl-[1,2,4]oxa-diazol-5-yl)-propyl]-amine as described before. Form 2 is characterised by having an XRPD pattern with signals substantially as listed in Table 1.

The present invention provides the polymorph Form 2 of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

[3-(4-Methoxy-2-methyl-phenyl)-2,5-dimethyl-pyrazolo[1,5-a]pyrimidin-7-yl]-[(S)-1-(3-methyl-[1,2,4]oxadiazol-5- yl)-propyl]-amine may be also designated from now on as compound of Formula (I).

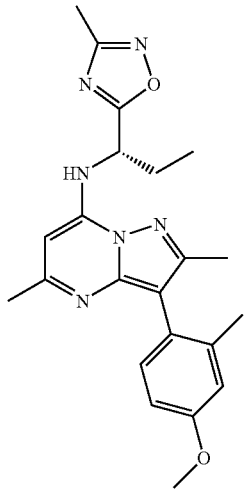

The polymorph Form 2 of the compound of Formula (I) of the present invention is a free base.

The polymorph Form 2 of the compound of Formula (I) of the present invention has been characterised as reported below in the Examples.

The present invention additionally provides compositions comprising the compound of the present invention and a pharmaceutically acceptable carrier.

Further embodiments include methods of treating a disorder in a mammal characterized by abnormal levels of CRF, comprising administering to the mammal a therapeutically effective amount of the compound of the present invention. Accordingly, the present invention further provides methods of treating anxiety or depression or irritable bowel syndrome in a mammal comprising administering to the mammal a therapeutically effective amount of the compound of the present invention.

Accordingly, the present invention further provides pharmaceutical compositions comprising polymorph Form 2 of [3-(4-methoxy-2-methyl-phenyl)-2,5-dimethyl-pyrazolo[1, 5-a]pyrimidin-7-yl]-[(S)-1-(3-methyl-[1,2,4]oxadiazol-5-yl)-propyl]-amine of Formula (I) and a pharmaceutically acceptable carrier.

A "pharmaceutically acceptable carrier" refers to media generally accepted in the art for the delivery of biologically active agents to animals, in particular, mammals.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Remington's Pharmaceutical Sciences, 17th ed., Mack Publishing Company, Easton, Pa., 1985, which is incorporated herein by reference in its entirety The present invention also includes methods of treating a disorder characterized by abnormal levels of corticotropin releasing factor in a mammal by administering to the mammal a therapeutically effective amount of the compound of the present invention, or a composition containing the compound of the present invention. According to some embodiments, the disorder can be characterized by elevated levels of corticotropin releasing factor. In some embodiments, the disorder affects the central nervous system. Example disorders of the central nervous system that can be treated according to the methods described herein include anxiety or depression.

In other embodiments, the disorder affects peripheral systems. Accordingly, an example of a treatable disorder of the peripheral systems according to the methods described herein is irritable bowel syndrome.

CRF receptor antagonists of the present invention may demonstrate activity at the CRF receptor site, and may be used as therapeutic agents for the treatment of a wide range of disorders or illnesses including endocrine, psychiatric, and neurological disorders or illnesses. More specifically, CRF receptor antagonists of the present invention may be useful in treating physiological conditions or disorders arising from the hypersecretion of CRF. Because CRF is believed to be an important neurotransmitter that activates and coordinates the endocrine, behavioral and automatic responses to stress, CRF receptor antagonists of the present invention may be useful in the treatment of neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease and G.I. motility), pain, Cushing's disease, infantile spasms, epilepsy and other seizures in both infants and adults, and various substance abuse and withdrawal (including alcoholism).

Within the context of the present invention, the following terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "psychotic disorder" includes:—

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9). The compounds of the present invention including salts and pharmaceutically acceptable solvates thereof may also be of use in the treatment of the following disorders:—

Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

Anxiety disorders including Social Anxiety Disorder, Panic Attack, Agoraphobia, Panic Disorder, Agoraphobia Without History of Panic Disorder (300.22), Specific Phobia (300.29) including the subtypes Animal Type, Natural Environment Type, Blood-Injection-Injury Type, Situational Type and Other Type), Social Phobia (300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder and Anxiety Disorder Not Otherwise Specified (300.00):

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition; and Substance-Induced Sleep Disorder including the subtypes Insomnia Type, Hypersomnia Type, Parasomnia Type and Mixed Type:

Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; and Eating Disorder Not Otherwise Specified (307.50):

Autistic Disorder (299.00); Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9):

Enhancement of cognition including the treatment of cognition impairment in other diseases such as schizophrenia, bipolar disorder, depression, other psychiatric disorders and psychotic conditions associated with cognitive impairment, e.g. Alzheimer's disease: and Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

All of the various forms and sub-forms of the disorders mentioned herein are contemplated as part of the present invention.

The term "therapeutically effective amount" refers to an amount of the compound of the present invention effective to reduce or eliminate at least one symptom of a disorder that the compound was used to treat.

The compound of the present invention can be administered to treat the above disorders by any suitable means that allows the compound to contact the site of action, such as a CRF receptor, in the body of a mammal. The compound can be administered by any conventional means available for use in conjunction with pharmaceuticals either as an individual therapeutic agent or in combination with other therapeutic agents. The compound of the present invention can be administered alone, or in combination with a pharmaceutical carrier selected on the basis of the chosen route of administration and standard pharmaceutical practice.

The dosage of the compound of the present invention for administration varies depending on several factors such as the pharmacodynamic character of the particular compound, and its mode and route of administration; the recipient's age, weight, and health; nature and extent of symptoms; kind of concurrent treatment; frequency of treatment; and desired effect. For use in the treatment of the above diseases or conditions, the salts of this invention can be orally administered daily at a dosage of the active ingredient (e.g. a salt of Formula I) of about 0.002 to about 200 mg/kg of body weight. For example, a dose of about 0.01 to about 10 mg/kg can be divided into smaller doses and administered one to four times a day. Alternatively, sustained release formulations can be effective in obtaining the desired pharmacological effect.

Dosage forms (compositions) suitable for administration can contain from about 1 mg to about 200 mg of active ingredient per dosage unit. In these pharmaceutical compositions, the active ingredient (e.g. polymorph Form 2 of formula (I)) can be present in an amount of about 0.5 to 95% by weight based on the total weight of the composition.

The active ingredient (e.g., polymorph Form 2 of formula (I)) can be administered orally in solid dosage forms such as capsules, tablets and powders, or in liquid forms such as elixirs, syrups, and/or suspensions. The compound of this invention can also be administered parenterally in sterile liquid dose formulations Gelatin capsules can be used to contain the active ingredient and a suitable carrier such as, but not limited to, lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can also contain colouring or flavouring agents to increase patient acceptance.

Typically, water, pharmaceutically acceptable oils, saline, aqueous dextrose, and related sugar solutions and glycols, such as propylene glycol or polyethylene glycol, are suitable carriers for parenteral solutions. Solutions for parenteral administration can contain, for example, a water soluble salt of the active ingredient and suitable stabilizing agents. Antioxidizing agents, such as sodium bisulfite, sodium sulfite, or ascorbic acid, either alone or in combination, can act as suitable stabilizing agents.

Also suitable as stabilizing agents are citric acid and its salts, and EDTA. In addition, parenteral solutions can contain preservatives such as, for example, benzalkonium chloride, methyl- or propyl-paraben, and chlorobutanol.

EXAMPLE

Abbreviations:
DCM: Dichloromethane
DIC: N,N'-Diisopropylcarbodiimide
DMF: Dimethylformamide HOBT: 1-Hydroxybenzotriazole DM water: demineralised water Intermediate 1

Preparation and Characterisation of Polymorph Form 1 of the Compound of Formula (I)

Polymorph Form 1 of the compound of Formula (I) may be prepared according to the following Scheme, as reported in WO 2006/044958:

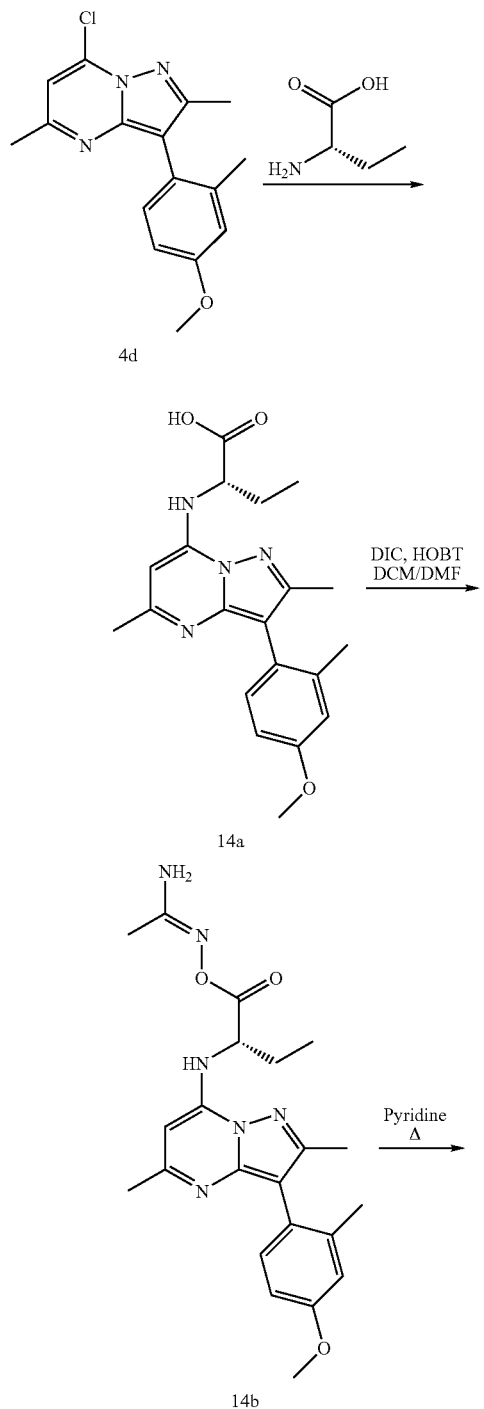

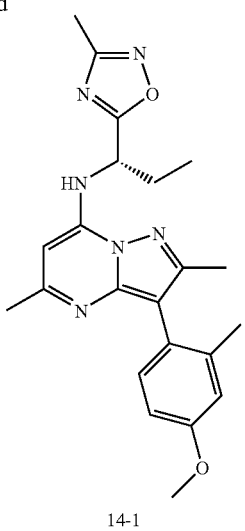

14-1

Step 14A:

A suspension of sodium bicarbonate (28.7 g) and (S)-2-aminobutyric acid (21.7 g) in water (250 mL) was added to a solution of 4d (prepared according to the method disclosed in WO 2006/044958) (39.7 g) in dioxane (250 mL). The mixture was stirred and heated to reflux (102° C. bath) for 14 hr. The mixture was cooled to RT, then concentrated HCl (16 mL) was added over 10 min to final pH 4.5. A copious white precipitate formed. The mixture was concentrated to a weight of about 250 g, then the residue was subjected to co-evaporation with several portions of ethyl acetate, resulting in a thick, pasty aqueous slurry. The mixture was filtered, and the filter cake was washed with water (350 mL). The filter cake was then dried under vacuum at 35° C., yielding compound 14a (45.2 g) as a white solid.

Step 14B:

Cmpd 14a (10 g) was suspended in toluene (50 mL) and evaporated to dryness. Dry DCM (100 mL) was added followed by HOBT (4.8 g) and acetamide oxime (2.7 g.) Anhydrous DMF (11 mL) was added, then the reaction mixture was stirred and cooled in an ethylene glycol/dry ice bath to an internal temperature of −15.5° C. under a nitrogen atmosphere. DIC (5.3 mL) was then added via syringe. The reaction mixture was stirred and allowed to warm over 2 hr, at which time the internal temperature was +16.5° C. The solvents were evaporated, then ethyl acetate (150 mL) was added and the mixture was washed twice with saturated aq. sodium bicarbonate, once with 10% aq. potassium dihydrogen phosphate, and finally with brine. The ethyl acetate layer was dried over sodium sulfate, filtered, and concentrated to provide crude Cmpd 14b.

Step 14C:

Pyridine (50 mL) was added to Cmpd 14b from Step 14B, then the mixture was heated under nitrogen at 100° C. for 4 hr. The resulting solution was allowed to cool, the solvent was evaporated, and the residue was co-evaporated twice with ethyl acetate and once with heptane. The residue was taken up in 50 mL ether, then filtered to remove DIU, rinsing with several portions of ether. The filtrate was evaporated, then the residue was chromatographed on silica gel, eluting with 2:1 hexane/ethyl acetate to provide the partially purified Cmpd 14-1 as a slightly yellow foam. The foam was co-evaporated once with heptane, then 5:1 heptane/ethyl acetate (60 mL) was added, and the resulting slurry was stirred at RT for 24 hr.

The solid was filtered and rinsed with 10:1 heptane/ethyl acetate, providing 14-1 free base (7.3 g) as a white solid. The filtrate was concentrated and a second crop of 14-1 free base (0.7 g) was collected, also as a white solid.

The free base 14-1 (6.0 g) was dissolved in 80 mL acetone and cooled in an ethylene glycol/dry ice bath to −12° C. (internal). Hydrogen chloride (8.9 mL of a 2.0 M solution in ether) was added in one portion. The clear yellow solution was stirred for 1 min, then the solvent was evaporated. The residue was co-evaporated with two portions of acetone, then dried under vacuum to produce an amber foam. The foam was pulverized and then dried under vacuum at RT for 24 hr, providing the hydrochloride salt 14-1 (6.7 g) as an amorphous tan powder.

Characterisation of Polymorph Form 1 of the Compound of Formula (I)

Free Base 14-1 prepared as before shows the XPRD pattern (FIG. 4) and it was identified as Form 1 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

Table 1: XRPD angles and d spacings for [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine, Form 1.

TABLE 1

| Angle 2-Theta ° | d value Angstrom |
| --- | --- |
| 6.721 | 13.1397 |
| 8.361 | 10.5663 |
| 10.698 | 8.26247 |
| 11.757 | 7.52055 |
| 13.323 | 6.64016 |
| 15.112 | 5.85779 |
| 15.492 | 5.71491 |
| 15.959 | 5.54892 |
| 18.222 | 4.86461 |
| 18.965 | 4.67554 |
| 20.291 | 4.37294 |
| 21.428 | 4.14338 |
| 21.974 | 4.04163 |
| 22.664 | 3.92018 |
| 24.002 | 3.70457 |
| 25.082 | 3.54736 |
| 26.268 | 3.38993 |
| 26.941 | 3.30677 |
| 30.544 | 2.92437 |
| 31.289 | 2.85642 |

It will be recognised that spectra and diffraction data will vary slightly according to various factors such as the temperature, concentration and instrumentation used. The skilled person will recognise that XRPD peak positions are affected by differences in sample height. The peak positions quoted herein are thus subject to a variation of +/−0.15 degrees 2-theta.

X-Ray Powder Diffraction

X Ray Powder Diffraction (XRPD) analysis was performed on Bruker D5005, using Sol-X detector. The acquisition conditions were: radiation: Cu Kα, generator tension: 40 kV, generator current: 50 mA, start angle: 2.0 °2θ, end angle: 45.0 °2θ, step size: 0.02 °2θ, time per step: 0.5 seconds. The sample was prepared on zero background sample holder.

Raman Spectroscopy

Instrument Configuration: Kaiser RXN1 Kaiser Optical System Micro Raman. Sample on Al sample pan, laser I=785 nm.

Differential Scanning Calorimetry (DSC)

Instrument configuration: PE DSC 7, not ermetic sample pan, run @10K/min to 150° C., sample 1.5-5 mg.

Example 1

Synthesis and Characterisation of Polymorph Form 2 of the Compound of Formula (I)

| HPLC method | |
| --- | --- |
| Column | Zorbax SB-C18(150 × 4.6 mm), 3.5 micron |
| Mobile Phase-A | 0.05% TFA(Aqueous) |
| Mobile Phase -B | 0.025% TFA(Acetonitrile) |
| Column temperature: | 40° C. |
| Flow rate | 1.0 ml/min |
| Wavelength of detection | 225 nm |
| Injection volume | 5 μl |
| Run time | 30 mins |
| Concentration | 0.3 mg/ml |
| Gradient program | Linear gradient |

| Time in min | Mobile phase-A(%) | Mobile phase-B (%) |
| --- | --- | --- |
| 0 | 75 | 25 |
| 25 | 5 | 95 |
| 29 | 5 | 95 |
| 30 | 75 | 25 |

| | |
| --- | --- |
| Post run time | 5 min |
| Retention time | Form 2 about 9 min |
| Diluent | Mobile Phase-A:Mobile Phase-B (1:1) |

Form 2 of [3-(4-methoxy-2-methyl-phenyl)-2,5-dimethyl-pyrazolo[1,5-a]pyrimidin-7-yl]-[(S)-1-(3-methyl-[1,2,4] oxadiazol-5-yl)-propyl]-amine was prepared as follows:

[3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine Form 1 (0.74 g) was slurried in 50% aqueous isopropanol (4 mL). The temperature was cycled between 0 and 40° C. for 24 hours, then the mixture stirred at ambient temperature for 3 days, then the temperature was cycled between 0 and 40° C. for 24 hours. The residual solid was filtered off and dried at ambient temperature to give 0.70 g of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine Form 2.

Preparation of Form 2 of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine was then repeated on large scale as follows.

Free Base 14-1 was prepared in an analogous way as described before, except for the lack of the chromatographic purification present in Step 14C. The formation and successive liberation of the mesylate salt afforded a desired compound with an high purity without the necessity of a chromatography.

Free Base 14-1 (2.48 kg, 6.10 Mol, chemical purity 90%) was stirred with n-Butyl acetate (12.5 L) for 30 to 45 minutes then Methane sulphonic acid (1.2 eq, 7.32 Mol, 703 g) was added. After stirring for 2-3 hrs at 25-30° C. the mixture was filtered. The solid was slurry washed with n-Butyl acetate (5 L) followed by Heptane (7.5 L). Then dried for 4-6 hrs at 50±5° C. under vacuum to give Mesylate salt (2.48 kg, chemical purity 97.37%).

The mesylate salt was stirred with DM water (12.5 L) for 15 to 30 minutes. Aq. ammonia was added to a pH of 9.0-10. The suspension was extracted with ethyl acetate (3×7.5 L).

then the combined extracts were washed with DM water (5 L) and 20% Brine solution (5 L). The organic solution was concentrated under vacuum at below 50±5° C., removing 85 to 90% of the solvent, then the residue cooled to 30±5° C. Heptane (15 L) was added and the mixture stirred for 2 to 3 hrs at 25-30° C. then 60 to 70% of the solvent was distilled off under vacuum at below 50±5° C. The mixture was cooled to 30±5° C., stirred for 1 to 2 hours, then filtered. The solid was slurry washed with Heptane (5 L) then dried under vacuum at below 50±5° C. to give Form 1 of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine (1.70 kg, chemical purity 99.34%).

A mixture of Form 1 (1.37 kg, 3.37 Mol, purity by HPLC 99.34%) of [3-(4-methoxy-2-methyl-phenyl)-2,5-dimethyl-pyrazolo[1,5-a]pyrimidin-7-yl]-[(S)-1-(3-methyl-[1,2,4] oxa-diazol-5-yl)-propyl]-amine and ethyl acetate (2.05 L) were heated up to 40 to 45° C. (a clear solution was observed). The solution was then cooled to 30±5° C. and Heptane (6.85 L) added before heating to 60±2.5° C. Form 2 of [3-(4-methoxy-2-methyl-phenyl)-2,5-dimethyl-pyrazolo[1,5-a] pyrimidin-7-yl]-[(S)-1-(3-methyl-[1,2,4]oxadiazol-5-yl)-propyl]-amine seed material prepared as described above (0.5% w/w) was added at 60±2.5° C. then the mixture was cooled to 40±2.5° C., then heated back to 50±2.5° C. when further seed material (0.5% w/w) was added. The resulting slurry was cooled to 30±5° C. and stirred for 12 hrs at 30±5° C. Heptane (2.74 L) was added and the mixture stirred for a further 12 hrs at 30±5° C. The slurry was filtered and the solid slurry washed with heptane (2.74 L). The solid was dried under vacuum at 50±5° C. for 8 hrs to give 0.97 kg of Form 2 of [3-(4-methoxy-2-methyl-phenyl)-2,5-dimethyl-pyrazolo [1,5-a]pyrimidin-7-yl]-[(S)-1-(3-methyl-[1,2,4]oxadiazol-5-yl)-propyl]-amine (HPLC purity 99.58%), which has been characterised as follows.

Characterisation of Polymorph Form 2 of the Compound of Formula (I)

Form 2 of [3-(4-methoxy-2-methyl-phenyl)-2,5-dimethyl-pyrazolo[1,5-a]pyrimidin-7-yl]-[(S)-1-(3-methyl-[1,2,4] oxadiazol-5-yl)-propyl]-amine shows the XPRD pattern (FIG. 1).

Table 2: XRPD angles and d spacings for [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine, Form 2.

TABLE 2

| Angle (2-Theta °) | d value (Angstrom) |
|---|---|
| 10.415 | 8.48651 |
| 12.125 | 7.29347 |
| 12.36 | 7.15526 |
| 13.177 | 6.7136 |
| 13.527 | 6.5406 |
| 15.121 | 5.85426 |
| 16.045 | 5.51918 |
| 16.331 | 5.42339 |
| 19.457 | 4.55852 |
| 20.133 | 4.40682 |
| 20.941 | 4.2386 |
| 21.28 | 4.1718 |
| 22.239 | 3.99412 |
| 22.823 | 3.89318 |
| 23.51 | 3.78098 |
| 24.714 | 3.59933 |
| 25.488 | 3.49186 |
| 26.261 | 3.39074 |
| 29.537 | 3.02169 |
| 27.858 | 3.19988 |

It will be recognised that spectra and diffraction data will vary slightly according to various factors such as the temperature, concentration and instrumentation used. The skilled person will recognise that XRPD peak positions are affected by differences in sample height. The peak positions quoted herein are thus subject to a variation of +/−0.15 degrees 2-theta.

X-Ray Powder Diffraction

X Ray Powder Diffraction (XRPD) analysis was performed on Bruker D5005, using Sol-X detector. The acquisition conditions were: radiation: Cu Kα, generator tension: 40 kV, generator current: 50 mA, start angle: 2.0 °2θ, end angle: 45.0 °2θ, step size: 0.04 °2θ, time per step: 1 second. The sample was prepared on zero background sample holder.

Raman Spectroscopy

Instrument Configuration: Kaiser RXN1 Kaiser Optical System Micro Raman. Sample on Al sample pan, laser l=785 nm.

Differential Scanning Calorimetry (DSC)

Instrument configuration: Q 1000 TA, not ermetic sample pan, run @10K/min to 150° C., N2 Flow=50 mL/min, sample 1.5-5 mg.

Example 2

Thermodynamic Relationship Between Form 1 and Form 2 of the Compound of Formula (I)

For a polymorphic substance, a property of particular interest is the relative thermodynamic stability of the polymorphs. The questions to be answered are the following:
a) whether two polymorphs are monotropic (one is more stable than the other at any temperature or enantiotropic (a transition temperature $(T_t)$ exists, below and above which the stability order is reversed; and
b) for an enantiotropic system, where $(T_t)$ lies.

The thermodynamic relationship between Form 1 and Form 2 of compound of Formula (I) was calculated using the melting data of polymorphs measured by DSC, according to what disclosed in: Lian Yu, *Journal of Pharmaceutical Science*, Vol. 84, No. 8, August 1995.

Based on DSC data (see reference article), Form 1 and Form 2 have a monotropic relationship and Form 2 may be considered the stable form (thermodynamically).

Taking samples of Form 1 and Form 2 as pure forms 1 and 2 respectively, and using the melting point and the ΔH obtainable by DSC data, it was possible to calculate the thermodynamic relationship and the transition temperature.

Form 1: T=100.09° C. & ΔH=75.46 J/g
Form 2: T=110.35° C. & ΔH=83.43 J/g

By solving the equation present in the cited article, the transition temperature corresponds to T=356° C. and it is greater than the previous two for Form 1 and Form 2 and $\Delta H_0<0$, $\Delta S_0<0$, then the conclusion is that the two polymorphic forms have a monotropic relationship.

Figure 7:
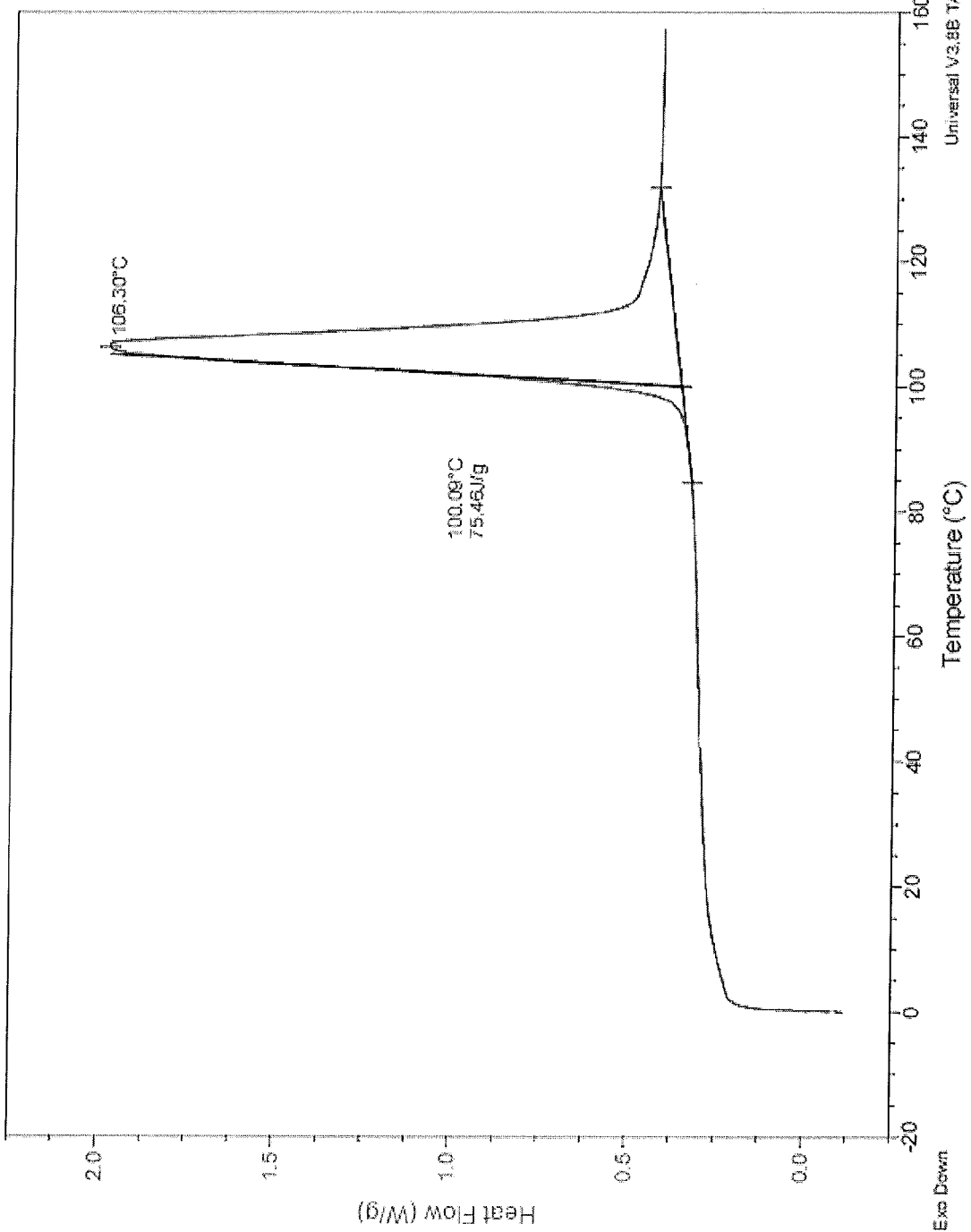
FIG. 7, a Differential Scanning Calorimetry (DSC) thermogram of a different sample of the polymorph Form 1.

The above calculation has been performed using DSC data for a different sample of polymorph Form 1 of compound of Formula (I), showing the Differential Scanning Calorimetry (DSC) thermogram of FIG. 7, obtained by the same method discussed above.

It should be recognized that the endotherm peak as measured is dependent under a number of factors including the machine employed, the rate of heating, the calibration standard, humidity and the purity of the sample used.

Figure 6:
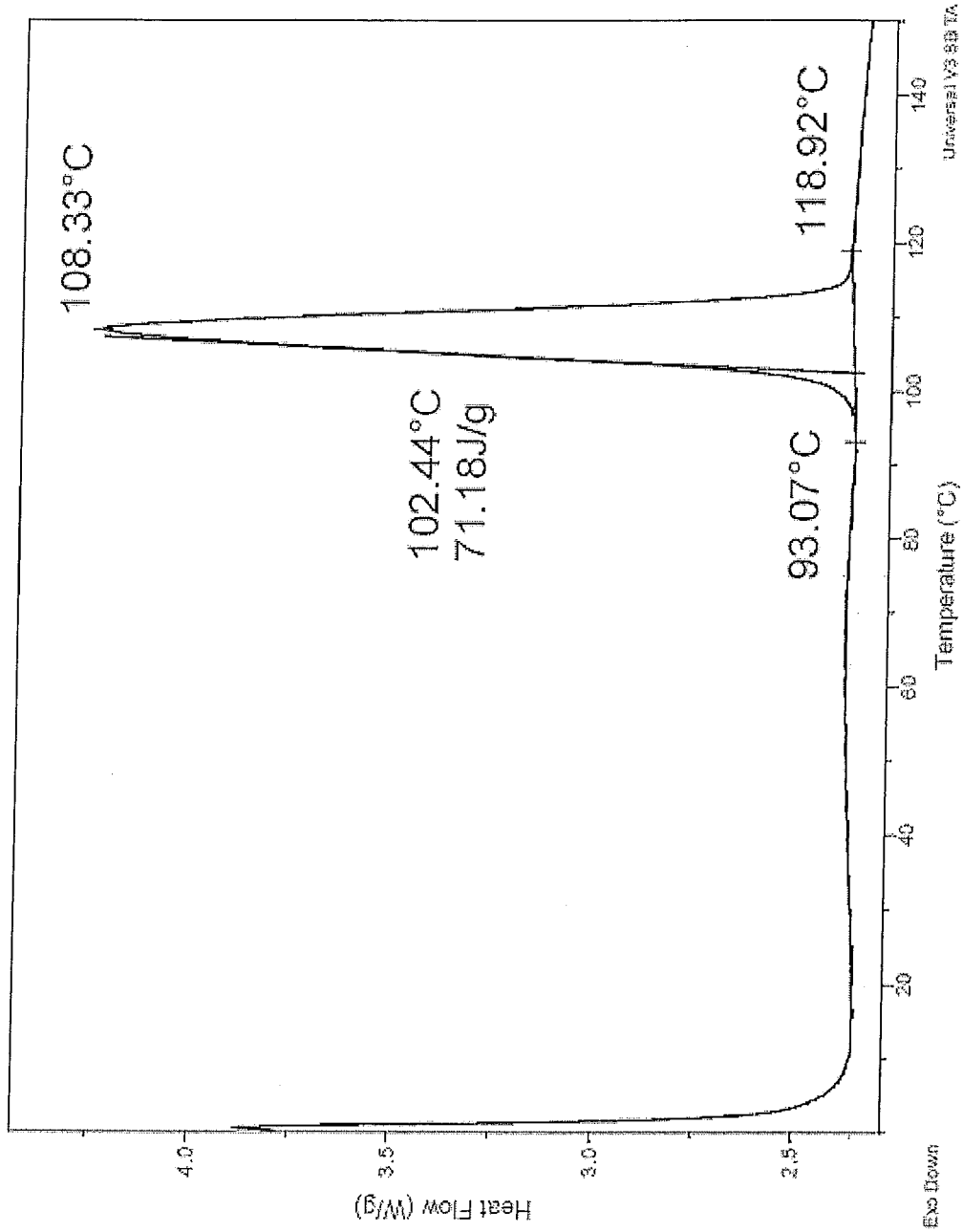
FIG. 6 shows a Differential Scanning Calorimetry (DSC) thermogram of Form 1 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

A similar calculation has been performed using the DSC data of polymorph Form 1 of compound of Formula (I) showed in FIG. 6, prepared according to the process described above.

Form 1: T=102.44° C. & ΔH=71.18 J/g
Form 2: T=110.35° C. & ΔH=83.43 J/g

The transition temperature is now corresponding to T=177° C., greater than the previous two for Form 1 and Form 2, and $\Delta H_0 < 0$, $\diamond S_0 < 0$, confirming again the monotropic relationship between the two polymorphic forms.

Example 3

Conversion of Mixture of the Two Polymorphs of the Compound of Formula (I) to Form 2

A saturated solution in ethyl acetate/heptane=½ of Form 1 of compound of Formula (I) (25 mg in 400 μL) was prepared.

20.4 mg of solid Form 1 of compound of Formula (I) were mixed with 21.3 mg of solid Form 2 of compound of Formula (I). That solid mixture was added to the above saturated solution. The slurry so obtained was stirred at RT one day long. The day after, the solid and liquid phase were separated by centrifugation, and the solid was simply left on air in order to dry and then examined by XPRD.

The analysis showed that the solid was only constituted by Form 2 of compound of Formula (I).

Example 4

Alternative Preparation of Form 2 of the Compound of Formula (I)

Free Base 14-1 was prepared using a slightly modified process from 14a. The revised reactions conditions led to the formation of lower amounts of related impurities so, instead of mesylate salt formation and successive liberation, the desired compound was obtained directly from the work-up of the reaction from 14b without the need for additional purification. The crude purity was sufficient to provide Form 2 of acceptable chemical purity when using a direct seeded crystallisation procedure. The advantage of this alternative crystallisation is that the desired Form 2 can be prepared direct from solution by seeding with material of the appropriate form, thus allowing for better control of the physical characteristics of the final material if required in the future.

To a mixture of DCM (278 L) and 14a (55.5 kg) were added: HOBT (26.5 kg), acetamidooxime (15.1 kg) and DMF (55.5 L) under nitrogen atmosphere. After stirring for 5 minutes the reaction mass was cooled to 0-5° C. A solution of DCC (40.5 kg) in DCM (278 L) was added over 4 hours at below 25° C. After completion of the addition, the reaction mass was stirred for 1.5 to 2 hrs at below 25° C. The reaction temperature was raised to 25-35° C. and the reaction mixture was filtered, washing the residue with DCM (111 L). The combined DCM layer was washed with 5% bicarbonate solution (3×280 L) followed by DM water (166.5 L) and finally with 5% Brine solution (166.5 L). The organic layer was concentrated under vacuum below 50° C. Toluene (278 L) was added and the reaction temperature was raised to reflux for 3 to 4 hrs. The reaction was cooled to 30-35° C. and extracted with 5N HCl (3×111 L). The combined aqueous were treated with Charcoal (5 kg) and stirred for 15 to 30 minutes then the reaction mixture was filtered through Celite and washed with 5N HCl (111 L). The combined aqueous layers from the Celite filtration were added to aqueous ammonia (500 L) and ethyl acetate (278 L) cooled to 0-10° C. The layers were separated and the aqueous layer was extracted with ethyl acetate (2×278 L). The combined organic layers were washed with DM water (278 L) followed by 20% brine solution (278 L). 80 to 85% solvent was distilled from the reaction mixture under vacuum at below 55° C. The reaction mass was cooled to 30±5° C. and heptane (555 L) was added. After stirring for 1 to 2 hrs, 75 to 85% of solvent was distilled from the reaction mixture under vacuum at below 55° C. The reaction mass was cooled to 30±5° C. and the reaction mass was filtered, washing with Heptane (100 L). The material was dried under vacuum for 4-6 hrs to give free base 14.1 (50.7 kg).

Free base 14.1 (50.7 kg) was dissolved with ethyl acetate (253.5 L). Heptane was added (1116 L) and the mixture was stirred for 15-20 hrs. The reaction mixture was then filtered through a Nutsche filter and washed with ethyl acetate/heptane mixture (1:5) (36 L). The filtrate was then concentrated under vacuum at below 50±5° C. until removal of 85 to 90% of the solvent. The reaction was then cooled at 30±5° C. and Heptane (278 L) was added. After stirring for 1 to 2 hrs at 25-30° C., 75-85% of the solvent was removed under vacuum below 50±5° C. Then the temperature is kept at 30±5° C. and heptane (167 L) was added and the reaction mass was stirred for 15 to 30 minutes and then filtered. The final solid was washed with Heptane (167 L) and dried to give Form 1 of [3-(4-methoxy-2-methyl-phenyl)-2,5-dimethyl-pyrazolo[1,5-a]pyrimidin-7-yl]-[(S)-1-(3-methyl-[1,2,4]-oxadiazol-5-yl)-propyl]-amine (41.1 kg, chemical purity 93.6%).

A mixture of Form 1 (41.1 kg) and isopropyl alcohol (123.5 L) was heated to 45-55° C., producing a clear solution. The solution was filtered then the temperature was kept at 30-40° C. and seeds of Form 2 of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine were added. The stirring was continued for 5-6 hrs, then the suspension was cooled to 5-15° C. and stirred for 1-2 hrs. The suspension is then filtered and washed with cold isopropyl alcohol and dried under vacuum at 50±5° C. to give 30.2 kg of Form 2 of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine (HPLC purity 98.63%).

Example 5

Recrystallisation of Form 2 of the Compound of Formula (I)

If the purity of the Form 2 prepared by the process described in Example 4 does not meet the required specification, a further seeded recrystallisation to give Form 2 can be carried out.

3 kg of Form 2 of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine (prepared according to Example 4, HPLC purity 98.63%,) was added to isopropyl alcohol (9 L) and stirred for 5 to 10 minutes. The reaction mixture temperature was then raised to 52.5±2.5° C. and a clear solution was obtained. The temperature was reduced to 35±5° C. and seeds of Form 2 of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine were added. The reaction mixture was then stirred for 2-3 hrs. at 30±5° C. Then the reaction mixture was cooled to 0° C.+5° C. and stirred for 1-2 hrs. The suspension was then filtered and washed with cold Isopropyl alcohol and dried under vacuum at 50° C. to give 2.4 kg of Form 2 of [3-(4-methoxy-2-methyl-phenyl)-2,5-dimethyl-pyrazolo[1,5-a]pyrimidin-7-yl]-[(S)-

Figure 8:
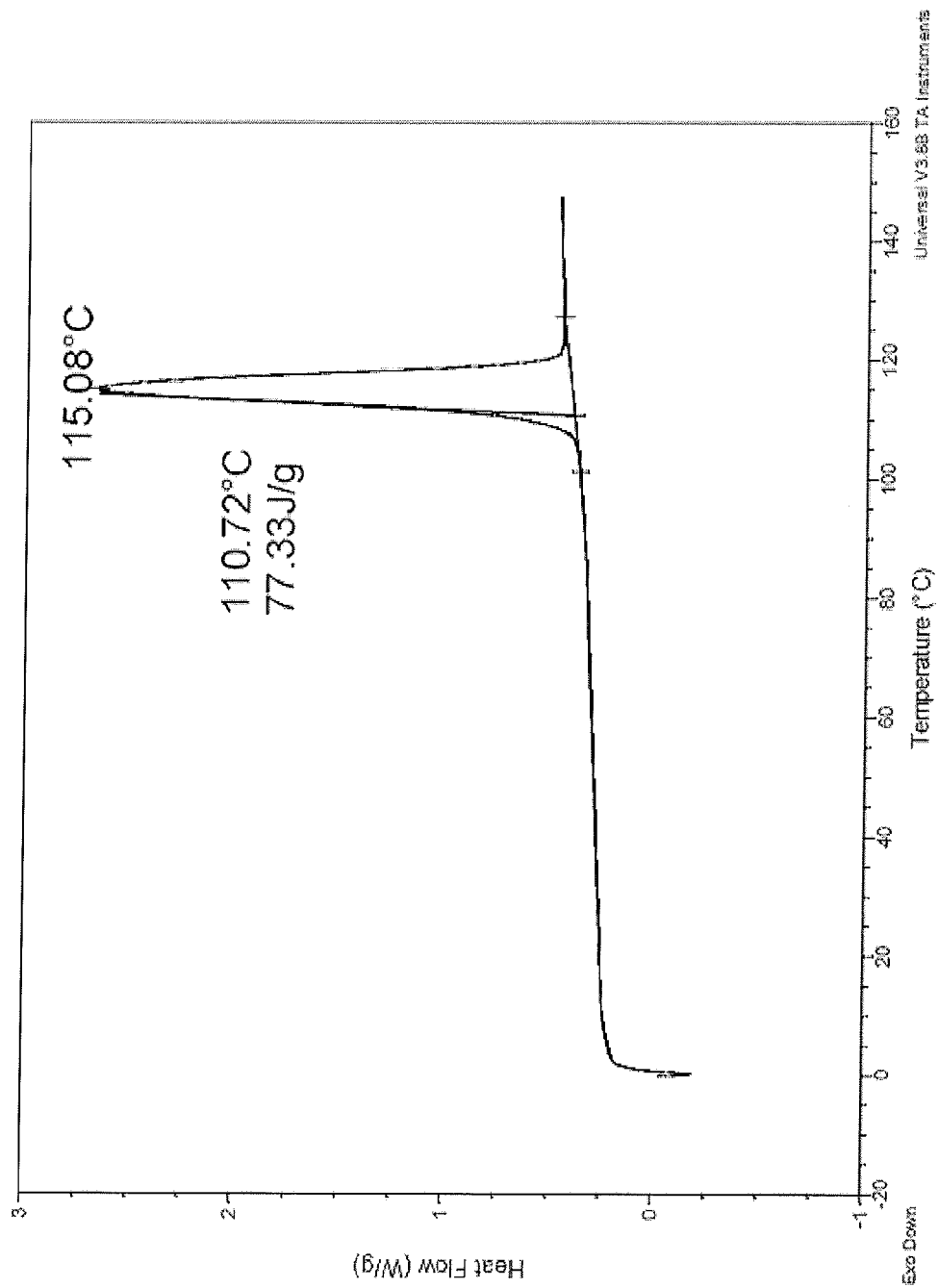
FIG. 8, a Differential Scanning Calorimetry (DSC) thermogram of a different sample of the polymorph Form 2.

1-(3-methyl-[1,2,4]-oxadiazol-5-yl)-propyl]-amine (HPLC purity 99.73%), which shows the DSC of FIG. 8.

Example 6

Comparison of Xrpd Data of Polymorphs Form 1 and Form 2 of the Compound of Formula (I)

| Form 1 | | Form 2 | |
|---|---|---|---|
| 2θ | d value | 2θ | d value |
| 6.721 | 13.1397 | | |
| 8.361 | 10.5663 | | |
| | | 10.415 | 8.48651 |
| 10.698 | 8.26247 | | |
| 11.757 | 7.52055 | | |
| | | 12.125 | 7.29347 |
| | | 12.36 | 7.15526 |
| | | 13.177 | 6.7136 |
| 13.323 | 6.64016 | | |
| | | 13.527 | 6.5406 |
| 15.112 | 5.85779 | | |
| | | 15.121 | 5.85426 |
| 15.492 | 5.71491 | | |
| 15.959 | 5.54892 | | |
| | | 16.045 | 5.51918 |
| | | 16.331 | 5.42339 |
| 18.222 | 4.86461 | | |
| 18.965 | 4.67554 | | |
| | | 19.457 | 4.55852 |
| | | 20.133 | 4.40682 |
| 20.291 | 4.37294 | | |
| | | 20.941 | 4.2386 |
| 21.428 | 4.14338 | | |
| | | 21.28 | 4.1718 |
| | | 22.239 | 3.99412 |
| 21.974 | 4.04163 | | |
| 22.664 | 3.92018 | | |
| | | 22.823 | 3.89318 |
| | | 23.51 | 3.78098 |
| 24.002 | 3.70457 | | |
| | | 24.714 | 3.59933 |
| 25.082 | 3.54736 | | |
| | | 25.488 | 3.49186 |
| | | 26.261 | 3.39074 |
| 26.268 | 3.38993 | | |
| 26.941 | 3.30677 | | |
| | | 27.858 | 3.19988 |
| | | 29.537 | 3.02169 |
| 30.544 | 2.92437 | | |
| 31.289 | 2.85642 | | |

It is well known in the crystallography art that, for any given polymorph, the relative intensities of the diffraction peaks may vary due to preferred orientation resulting from factors such as crystal morphology. Where the effects of preferred orientation are present peak intensities are altered, but the characteristic peak positions of the polymorph are unchanged.

The X-ray powder diffraction pattern of polymorph Form 2 as shown in FIG. 1 exhibits predominant peaks (expressed in degrees 2θ+/−0.15 degrees 2θ) at the following positions: 10.415, 12.125, 19.457, 20.941 and 23.51.

Figure 4:
FIG. 4 shows X-Ray powder diffraction data obtained for Form 1 of [3-(4-Methoxy-2-methyl-phenyl)-2,5-dimethyl-pyrazolo[1,5-a]pyrimidin-7-yl]-[(S)-1-(3-methyl-[1,2,4]oxa-diazol-5-yl)-propyl]-amine as described before. Form 1 is characterised by having an XRPD pattern with signals substantially as listed in Table 1.

The X-ray powder diffraction pattern of polymorph Form 1 as shown in FIG. 4 exhibits predominant peaks (expressed in degrees 2θ+/−0.15 degrees 2θ) at the following positions: 6.721, 11.757, 13.323, 18.222, 21.426 and 21.974.

Example 7

Comparison Raman Data of Polymorphs Form 1 and Form 2 of the Compound of Formula (I)

Figure 2:
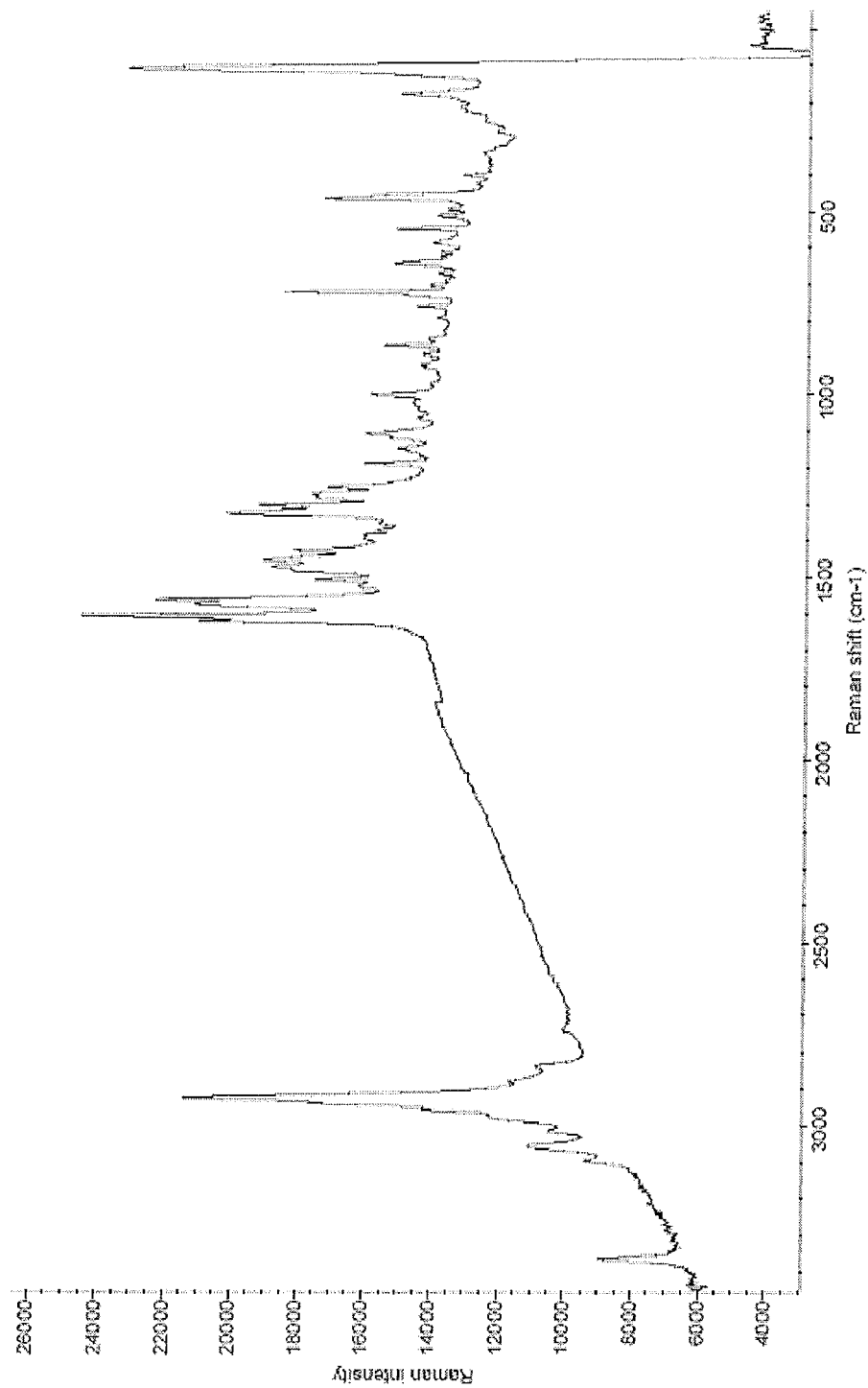
FIG. 2 shows the Raman spectrum of Form 2 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

The Raman spectrum of polymorph Form 2 as shown in FIG. 2 exhibits predominant peaks (expressed in $cm^{-1}$) at the following positions: 1606, 1561, 1506, 1323, 1301, 1279, 1271, 1253, 889 and 720.

Figure 5:
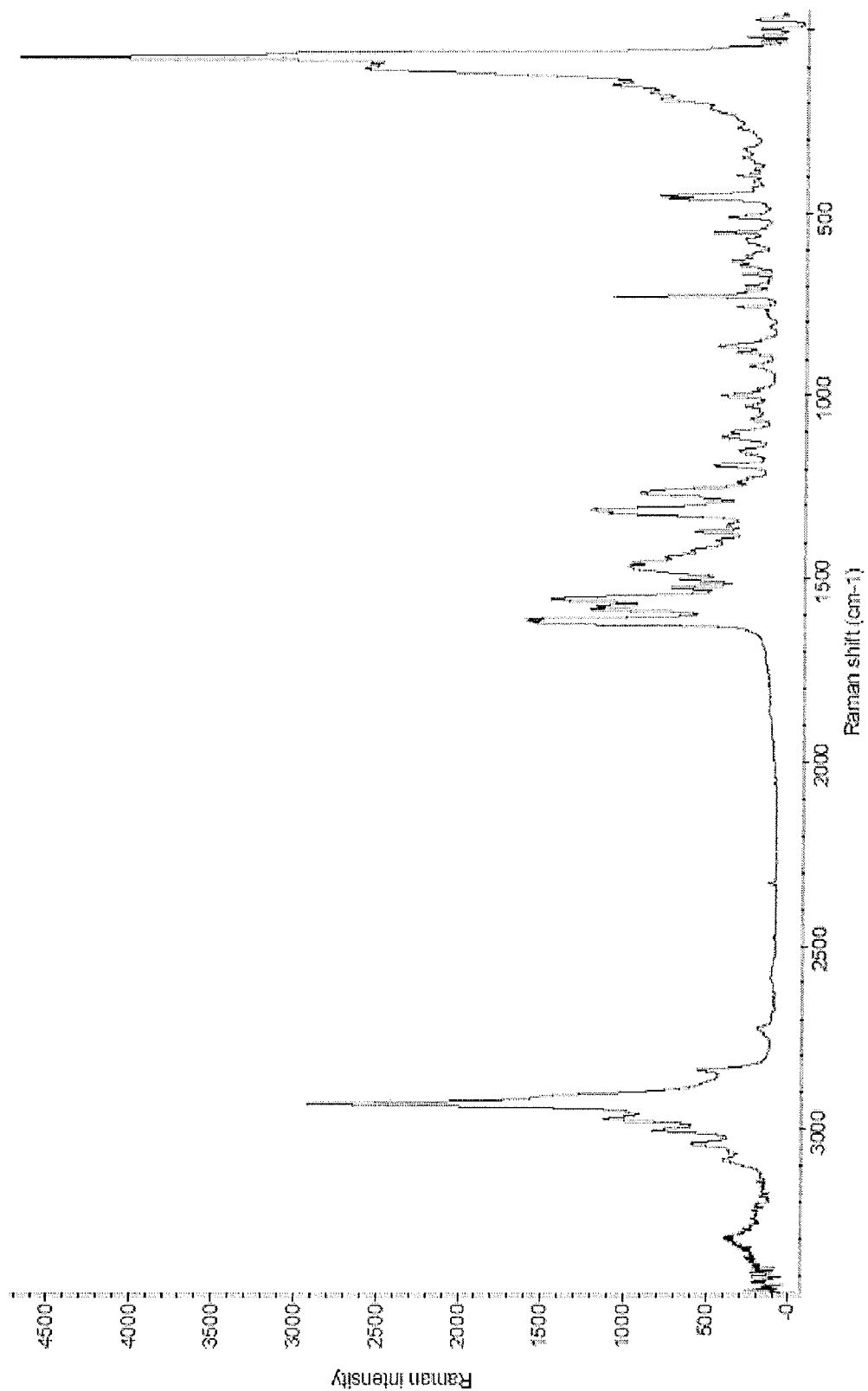
FIG. 5 shows the Raman spectrum of Form 1 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

The Raman spectrum of polymorph Form 1 as shown in FIG. 5 exhibits predominant peaks (expressed in $cm^{-1}$) at the following positions: 1619, 1611, 1581, 1574, 1555, 1525, 1502, 1319, 1311, 1264, 882 and 728.

Example 8

DSC Data of Polymorphs Form 1 and Form 2 of the Compound of Formula (I)

It should be recognized that the endotherm peak as measured is dependent under a number of factors including the machine employed, the rate of heating, the calibration standard, humidity and the purity of the sample used.

Figure 3:
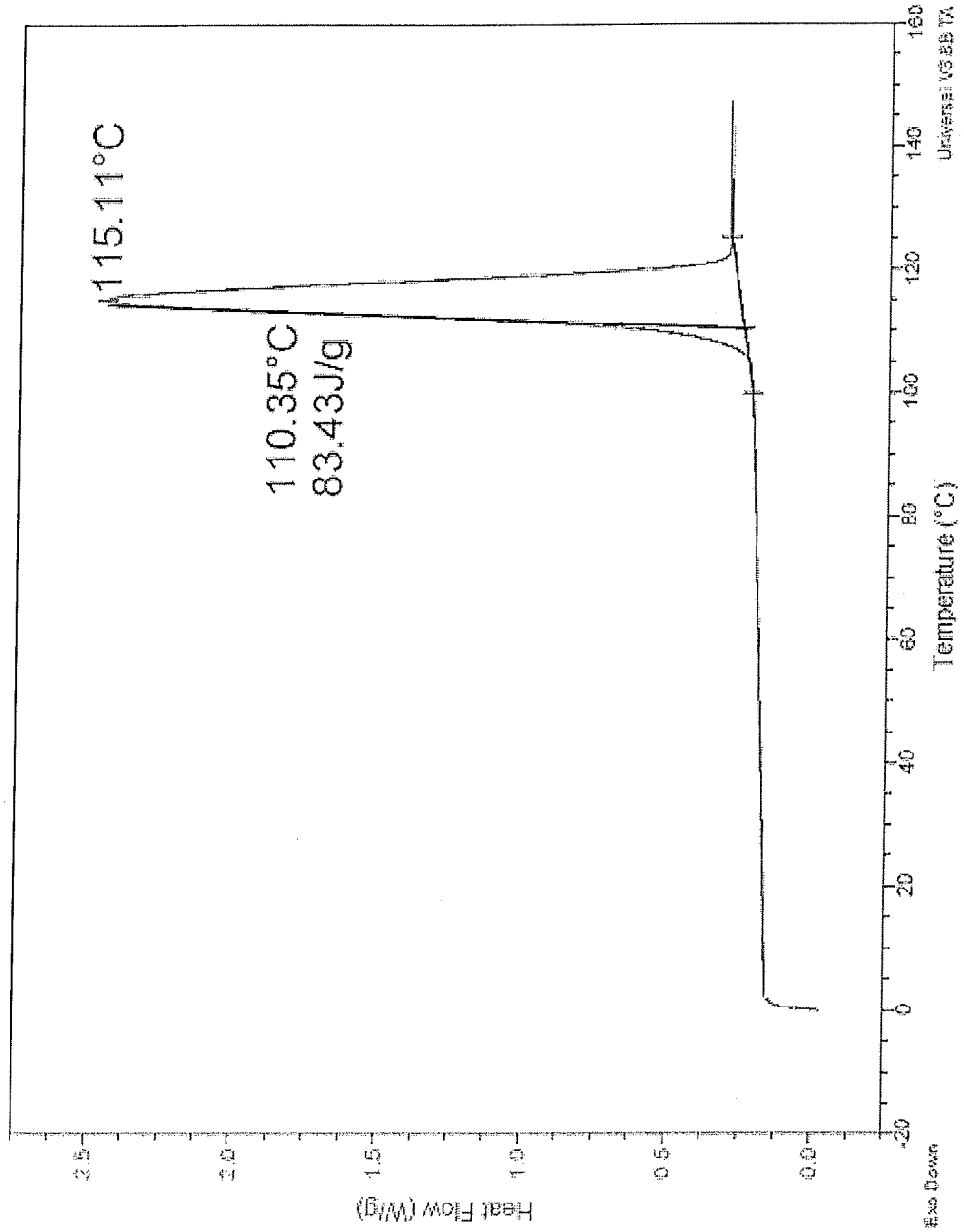
FIG. 3 shows a Differential Scanning Calorimetry (DSC) thermogram of Form 2 of [3-(4-Methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]amine.

As shown in FIG. 3, the polymorph Form 2 exhibits a predominant endotherm peak at about 115.1° C. and an onset at about 110.35° C.

As shown in FIG. 6, the polymorph Form 1 exhibits a predominant endotherm peak at about 108.3° C. and an onset at about 102.44° C.

As shown in FIG. 7, a different sample of the polymorph Form 1 exhibits a predominant endotherm peak at about 106.3° C. and an onset at about 100.09° C.

As shown in FIG. 8, a different sample of the polymorph Form 2 exhibits a predominant endotherm peak at about 115.08° C. and an onset at about 110.72° C.

Example 9

Illustrative Example of a Formulation Containing Polymorph Form 2 of the Compound of Formula (I)

The development of tablets containing polymorph Form 2 of compound of Formula (I) have been performed introducing a wet-granulation step to obtain granules with increased flow properties. This step involves the wet granulation of one or more components of the tablet formulation by means of a High Shear Granulator followed by drying phase and calibration.

The tablet was then formulated taking into account the technological properties of the granules (size, flowability, disintegrating and binding capacity of the final powder blend) and trying to assure a rapid dissolution of the drug, as final stage tablet was also coated by applying an aqueous film coating.

The excipients used were Mannitol and Microcrystalline cellulose (Avicel®) as diluent, Croscarmellose Sodium (AcDisol®) as disintegrant, Magnesium Stearate as lubricant, Sodium Lauryl Sulphate as wettability enhancer (surfactant), HPMC as binder and Opadry OY-S-28876 as coating agent.

The final composition of both granules and tablets are below reported 200 mg dose AFC (aqueous film coated) Tablets

| COMPONENT | AMOUNT (mg)/UNIT | % w/w |
|---|---|---|
| Form 2 64.0% Granule Correspond to: Form 2: 200.00 HPMC: 46.88 Sodium Lauryl Sulphate: 3.13 Sodium Croscarmellose: 9.38 Mannitol powder: 53.11 | 312.50 | 83.33 |
| MCC Avicel PH102 | 47.50 | 12.67 |
| Sodio Croscarmellose | 11.25 | 3.00 |
| Magnesium Stearate | 3.75 | 1.00 |
| Total core weight: | 375.00 | 100.00 |
| Opadry OY-S-28876 | 11.25 | 3.00 |
| Total weight: | 386.25 | 103.00 |

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular and preferred groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. Crystalline Form 2 of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine.

2. A composition comprising crystalline Form 2 of [3-(4-methoxy-2-methyl-phenyl)-2,5-dimethyl-pyrazolo[1,5-a]pyrimidin-7-yl]-[(S)-1-(3-methyl-[1,2,4]oxadiazol-5-yl)-propyl]-amine according to claim 1 and a pharmaceutically acceptable carrier.

* * * * *